United States Patent
Piantoni et al.

(10) Patent No.: US 11,376,165 B2
(45) Date of Patent: Jul. 5, 2022

(54) METHOD AND UNIT FOR FORMING AN ABSORBENT ARTICLE

(71) Applicant: GDM S.p.A., Bologna (IT)

(72) Inventors: Matteo Piantoni, Albino (IT); Marco Rosani, Vailarate (IT); Federico Toscani, Castelleone (IT); Andrea Duchini, Castelleone (IT); Mauro Pietralunga, Crema (IT); Aldo Fusarpoli, Offanengo (IT)

(73) Assignee: GDM S.P.A., Bologna (IT)

( * ) Notice: Subject to any disclaimer, the term of this patent is extended or adjusted under 35 U.S.C. 154(b) by 63 days.

(21) Appl. No.: 16/563,722

(22) Filed: Sep. 6, 2019

(65) Prior Publication Data

US 2020/0093648 A1    Mar. 26, 2020

(30) Foreign Application Priority Data

Sep. 20, 2018  (IT) .................. 102018000008752

(51) Int. Cl.
A61F 13/15    (2006.01)

(52) U.S. Cl.
CPC .. *A61F 13/15699* (2013.01); *A61F 13/15634* (2013.01); *A61F 13/15764* (2013.01)

(58) Field of Classification Search
CPC .......... A61F 13/15699; A61F 13/15764; A61F 13/15634; A61F 13/535
See application file for complete search history.

(56) References Cited

U.S. PATENT DOCUMENTS

| 6,811,642 B2 * | 11/2004 | Ochi ................ A61F 13/15634 156/213 |
| 10,259,185 B2 * | 4/2019 | Rosani ................ B31D 1/0075 |
| 2013/0240125 A1 | 9/2013 | Nelson et al. |
| 2015/0272786 A1 * | 10/2015 | Piantoni ............ A61F 13/15674 493/335 |

FOREIGN PATENT DOCUMENTS

| WO | 2004049989 A1 | 6/2004 |
| WO | 2012137100 A1 | 10/2012 |
| WO | 2013068868 A1 | 5/2013 |

OTHER PUBLICATIONS

Italian Search Report dated May 14, 2019 from counterpart Italian Application No. IT102018000008752.

* cited by examiner

*Primary Examiner* — George R Koch
*Assistant Examiner* — Christopher C Caillouet
(74) *Attorney, Agent, or Firm* — Shuttleworth & Ingersoll, PLC; Timothy Klima

(57) ABSTRACT

A method for forming an absorbent article including a first absorbent core and a second absorbent core which are superposed on each other, includes feeding a first supporting web along a first feed path in a first feed direction; placing a succession of first absorbent cores on the first supporting web at a preset spacing; feeding a second supporting web along a second feed path in a second feed direction; placing a succession of second absorbent cores on the second supporting web at the preset spacing; coupling the first supporting web to the second supporting web such that each first absorbent core is coupled to a corresponding second absorbent core in a composite web including the succession of first absorbent cores and the succession of the second absorbent cores interposed between the first supporting web and the second supporting web.

15 Claims, 3 Drawing Sheets

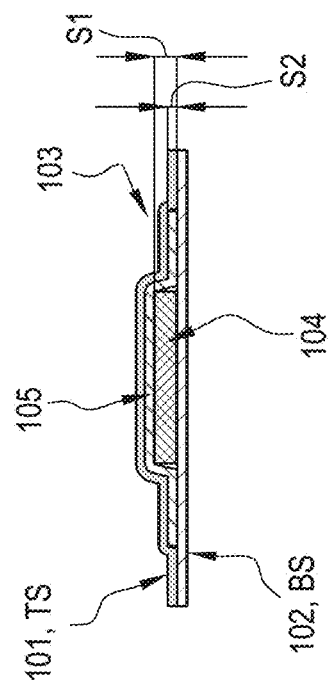
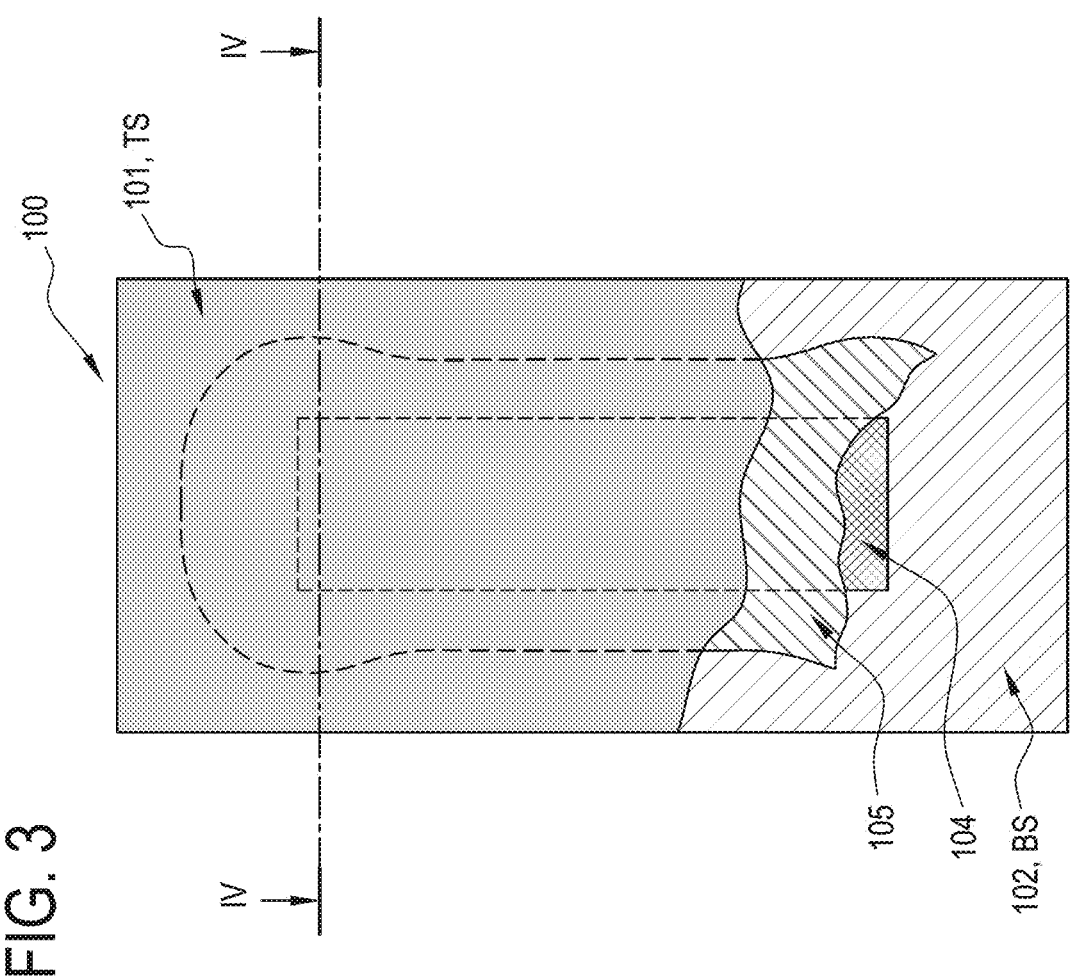
FIG. 3
FIG. 4

METHOD AND UNIT FOR FORMING AN ABSORBENT ARTICLE

This application claims priority to Italian Patent Application 102018000008752 filed Sep. 20, 2018, the entirety of which is incorporated by reference herein.

BACKGROUND OF THE INVENTION

This invention relates to a unit and a method for forming an absorbent article and, in particular, relates to a unit and a method for forming the multilayer absorbent cores or the main bodies of sanitary articles such as, for example, baby diapers, sanitary napkins or the like.

In this description, for simplicity, express reference is made to a diaper but without thereby limiting the scope of the invention.

As is known, diapers comprise an absorbent pad or padding which is normally enclosed between a permeable inner layer of non-woven fabric and an impermeable outer layer of polyethylene.

Market requirements have led diaper manufacturers to make nappies having an absorbent pad consisting of a double absorbent layer: a first, top layer or core, which is bigger and, in use, directed towards the wearer, and underneath, a second, smaller layer or core.

The relative position of the bigger absorbent core, on top of the smaller one and offset forward to a variable extent, is determined on the basis of the wearer's sex, age or special needs.

Document US20130240125 describes a pad similar to the one mentioned above and a method for making the pad.

According to what is described in that document, the smaller absorbent core, provided with a wrapping, is first placed on a polyethylene web, normally also called "backsheet", and the bigger core is then placed on top of the smaller one and the composite web thus formed is made to advance towards further processing stations.

One disadvantage of making these products that way, apart from the fact that the absorbent cores are placed in a wrapping, lies in the difficulty of positioning the bigger core on the smaller one and in keeping them in the right position as they advance on the carrier layer.

Moreover, since the small core is generally much thicker than the big core, it is very difficult to hold the big core against the small one and against the layer underneath that and to prevent loss of absorbent material from the cores, especially the big ones.

SUMMARY OF THE INVENTION

In this context, the main technical purpose of this invention is to propose a method and a unit for forming absorbent articles such as will be unaffected by the disadvantages mentioned above.

One aim of this disclosure is to propose a method and a unit for forming an absorbent article such as will allow precisely positioning the distinct absorbent cores making up the absorbent pad.

Another aim of this disclosure is to propose a method and a unit for forming absorbent articles such as will allow the absorbent material to be effectively retained during the forming process.

The technical purpose and aims specified are achieved by a unit for forming absorbent articles and by a method for forming absorbent articles as disclosed herein.

According to one aspect of it, this disclosure regards a method for forming an absorbent article of the type comprising a first, small absorbent core and a second, big absorbent core, placed on top of each other.

According to one aspect of it, this disclosure regards a method for forming an absorbent article comprising a step of feeding a first supporting web along a first feed path in a first feed direction and a step of placing a succession of first absorbent cores on the first supporting web at a preset spacing P.

The method comprises a step of feeding a second supporting web along a second feed path in a second feed direction and a step of placing a succession of second absorbent cores on the second supporting web at the spacing P.

According to one aspect of it, the disclosure regards a method for forming an absorbent article comprising a step of coupling the first supporting web to the second supporting web in such a way that each first absorbent core is coupled to a corresponding second absorbent core in a composite web comprising the succession of first absorbent cores and the succession of the second absorbent cores interposed between the first supporting web and the second supporting web.

Advantageously, the absorbent cores are first attached to or positioned on a respective supporting web and then the distinct webs provided with the respective absorbent cores are joined to each other to form a composite web.

According to one aspect of it, the disclosure regards a forming method comprising a step of compressing the first absorbent cores before the step of placing the succession of first absorbent cores on the first supporting web.

According to one aspect of it, the disclosure regards a forming method comprising a step of accelerating each first absorbent core before the step of placing the succession of first absorbent cores on the first supporting web, so as to space the first absorbent cores by the spacing P.

That way, thanks to an acceleration, which may be positive or negative, it is possible to space the absorbent cores by the required spacing as a function, for example, of the required size or form of the absorbent article to be made.

Preferably, the step of compressing the first absorbent cores is carried out before the step of accelerating each first absorbent core.

According to one aspect of it, the disclosure regards a forming method comprising a step of accelerating each second absorbent core before the step of placing the succession of second absorbent cores on the second supporting web, so as to space the second absorbent cores by the spacing P.

That way, thanks to an acceleration, which may be positive or negative, it is possible to space the second absorbent cores by the required spacing as a function, for example, of the required size or form of the absorbent article to be made.

Preferably, the step of compressing the second absorbent cores is carried out before the step of accelerating each second absorbent core.

According to one aspect of it, the disclosure regards a forming method wherein the step of placing the succession of second absorbent cores on the second supporting web at the spacing P is carried out while the second web moves along a curved line, specifically a circular arc.

That way, the absorbent core material not retained on the web does not drop onto the web and thus does not dirty it.

Preferably, the step of placing the succession of second absorbent cores on the second supporting web at the spacing P is carried out just before the step of coupling the first supporting web to the second supporting web.

According to one aspect of it, the disclosure regards a forming method wherein the first absorbent cores are smaller than the second absorbent cores, so that a big core is placed on a small core once the respective supporting webs have been coupled to each other.

According to one aspect of it, the disclosure regards a forming method wherein the first supporting web is the backsheet of an absorbent article and the second supporting web is the topsheet of the absorbent article.

Advantageously, according to one aspect of it, the disclosure regards a forming method wherein a small core is positioned on or attached to the backsheet of the absorbent article, a big core is coupled to the topsheet, and the backsheet and topsheet, with respective layers of the absorbent core, are joined to each other in such a way that each big core is positioned on a respective small core.

According to one aspect of it, this disclosure regards a unit for forming an absorbent article comprising a first system for feeding a first supporting web along a first feed path in a first feed direction; a first unit for forming and positioning the first absorbent core, disposed along the first feed path and comprising a first placing station for placing the first absorbent core on the first supporting web and comprising a first system for positioning the first core on the first supporting web at a spacing P, a second system for feeding a second supporting web along a second feed path in a second feed direction;

a second unit for forming and positioning the second absorbent core, disposed along the second feed path and comprising a second placing station for placing the second absorbent core on the second supporting web and comprising a second system for positioning the second absorbent core on the second supporting web at the preset spacing P; a coupling station for coupling the first supporting web to the second supporting web, disposed downstream of the first placing station and of the second placing station.

According to one aspect of the disclosure, the first and second absorbent cores overlap at least partly in the coupling station in such a way that each first absorbent core is coupled to a corresponding second absorbent core in a composite web comprising the succession of first absorbent cores and the succession of the second absorbent cores interposed between the first supporting web and the second supporting web.

According to one aspect of the disclosure, the forming unit comprises at least one compression system for compressing the absorbent cores and disposed upstream of the first placing station in a feed direction of the first absorbent cores.

According to one aspect of the disclosure, the first forming and positioning unit comprises a first accelerator for accelerating the first absorbent cores to space two consecutive first absorbent cores of the first absorbent cores by the spacing P.

According to one aspect of the disclosure, the second forming and positioning unit comprises at least a second compression system for compressing the second absorbent cores and disposed upstream of the second placing station in a feed direction of the second absorbent cores.

Preferably, the second forming and positioning unit comprises a second accelerator for accelerating the second absorbent cores to space two consecutive second absorbent cores of the second absorbent cores by the spacing P.

According to one aspect of the disclosure, the second feed system comprises a suction drum around which the second supporting web is at least partly wound and the second positioning system comprises at least one rotary carrier unit movable along a curved line, specifically a circular arc, substantially tangent to the suction drum in the placing station, the second positioning system releasing the second absorbent core onto the second supporting web along the curved line.

BRIEF DESCRIPTION OF THE DRAWINGS

Further features and advantages of this solution are more apparent in the non-limiting description of a unit and a method for forming absorbent articles, as illustrated in the accompanying drawings, in which:

FIG. 3 illustrates an example of an absorbent article obtainable with the forming method and unit according to this disclosure, in a schematic plan view;

FIG. 4 is a transverse cross section through the plane IV-IV of FIG. 3.

DESCRIPTION OF THE PREFERRED EMBODIMENTS

Figure 1:
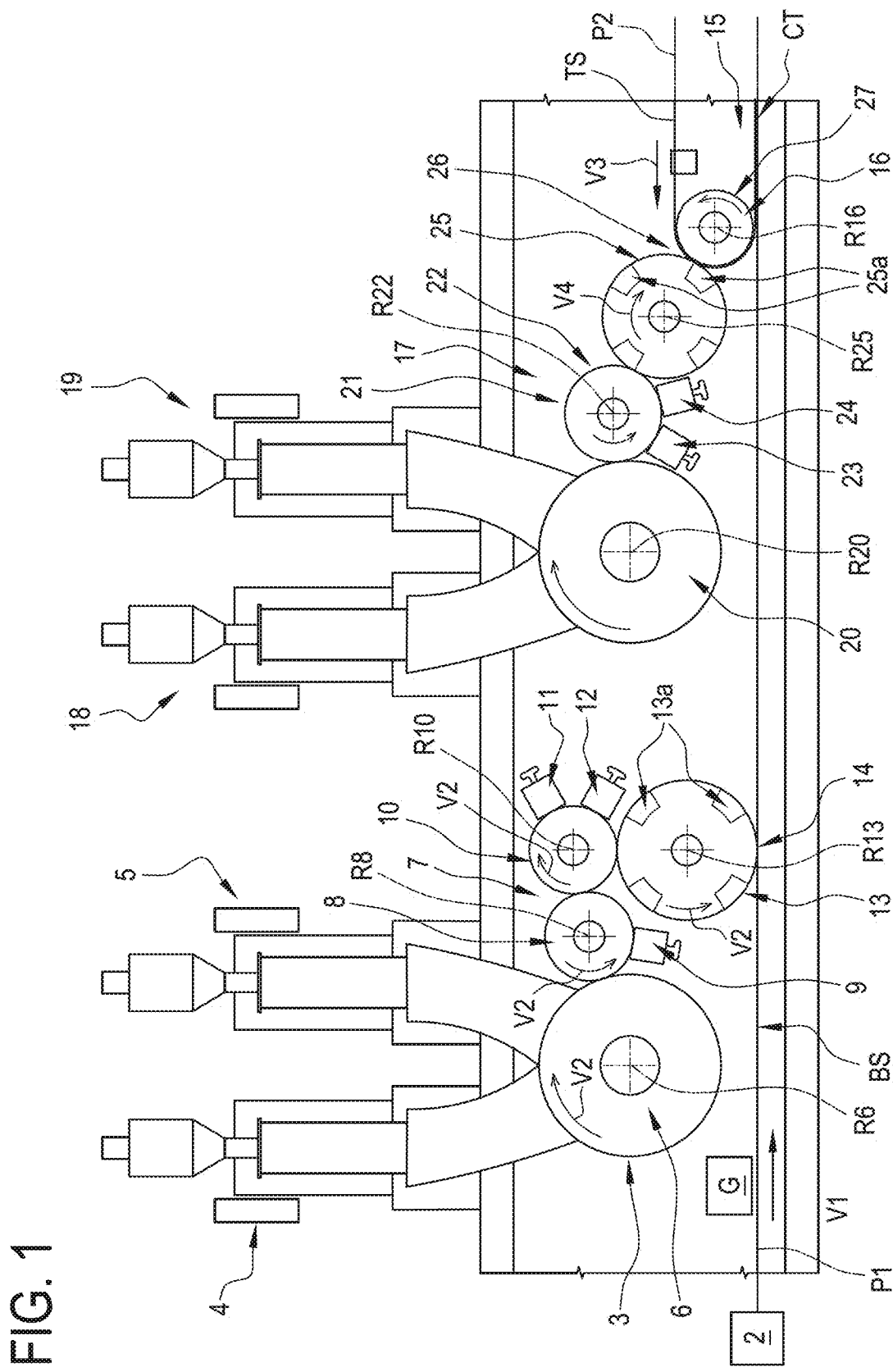
FIG. 1 illustrates a unit for forming absorbent articles according to this disclosure, in a schematic front view.

With reference in particular to FIG. 1, the numeral 1 denotes a unit for forming absorbent articles according to this disclosure.

FIGS. 3 and 4 illustrate an example of an absorbent article, denoted by the reference numeral 100, obtainable with the forming method and unit according to this disclosure.

The article 100 has a main direction of extension D, a front portion and a rear portion.

In a preferred embodiment, the main extension is the longitudinal one, that is the extension measured between the front portion and the rear portion of the article 100.

The article 100 comprises an inner, liquid-permeable layer 101, that is, the layer which, in use, is directed towards a generic wearer, and an outer layer 102.

The article 100 comprises an absorbent pad 103, sandwiched between the inner layer 101 and the outer layer 102.

The pad 103, made with a forming unit and method according to this disclosure, comprises a first absorbent core 104 and a second absorbent core 105, which is bigger than the first absorbent core 104, the two being coupled to each other.

The two absorbent cores 104, 105 are made, for example, from an absorbent material consisting of a mixture of cellulose pulp, also called "fluff", and superabsorbent material SAP.

In the embodiment illustrated by way of example, the absorbent core 105 is bigger than the absorbent core 104 in the main direction of extension D.

In the embodiment illustrated by way of example, the absorbent core 105 is bigger than the absorbent core 104 in the main direction of extension D.

The thickness S1 of the absorbent core 104, at right angles to the positioning plane of the pad 103, is greater than the thickness S2 of the absorbent core 105.

In a preferred embodiment, the thickness S1 is, for example, twice as large as the thickness S2.

Generally speaking, according to common practice in the trade, the first absorbent core 104 in a preferred embodiment is hereinafter also called "small core" and the second absorbent core 105 is hereinafter also called "big core".

In a preferred embodiment, the layer 101 is what is known as the "topsheet" of the article 100 and, in use, may be in direct contact with the wearer.

Usually, the layer 101 is preferably a length of non-woven fabric.

In the preferred embodiment, the outer layer 102 is impermeable and is what is known as the "backsheet" of the absorbent article 100—for example, a sheet of polyethylene.

The "topsheet" and the "backsheet" are joined to each other in known manner to define the outer container of the article 100.

In alternative embodiments, the inner layer 101 and the outer layer 102 are defined by lengths of non-woven fabric and form what is known as an "envelope" for the pad 103.

The forming unit 1 comprises a feed system, schematically represented as a block 2, for feeding a first supporting web BS.

For example, the feed system 2 comprises rotary drums not illustrated.

The web BS is intended to form the outer layer 102 of the absorbent article 100 and is, for example, an impermeable web that will form the backsheet of a diaper.

In an alternative use of the unit 1, the web BS is, for example, a web of non-woven fabric that may become part of an envelope for the absorbent pad 103.

In an alternative use of the unit 1, the web BS is, for example, a web of non-woven fabric that may become the topsheet of a diaper.

The web BS advances along a path P1, which is substantially straight in the example illustrated but which may have other shapes in alternative embodiments, in a direction V1.

Figure 2:
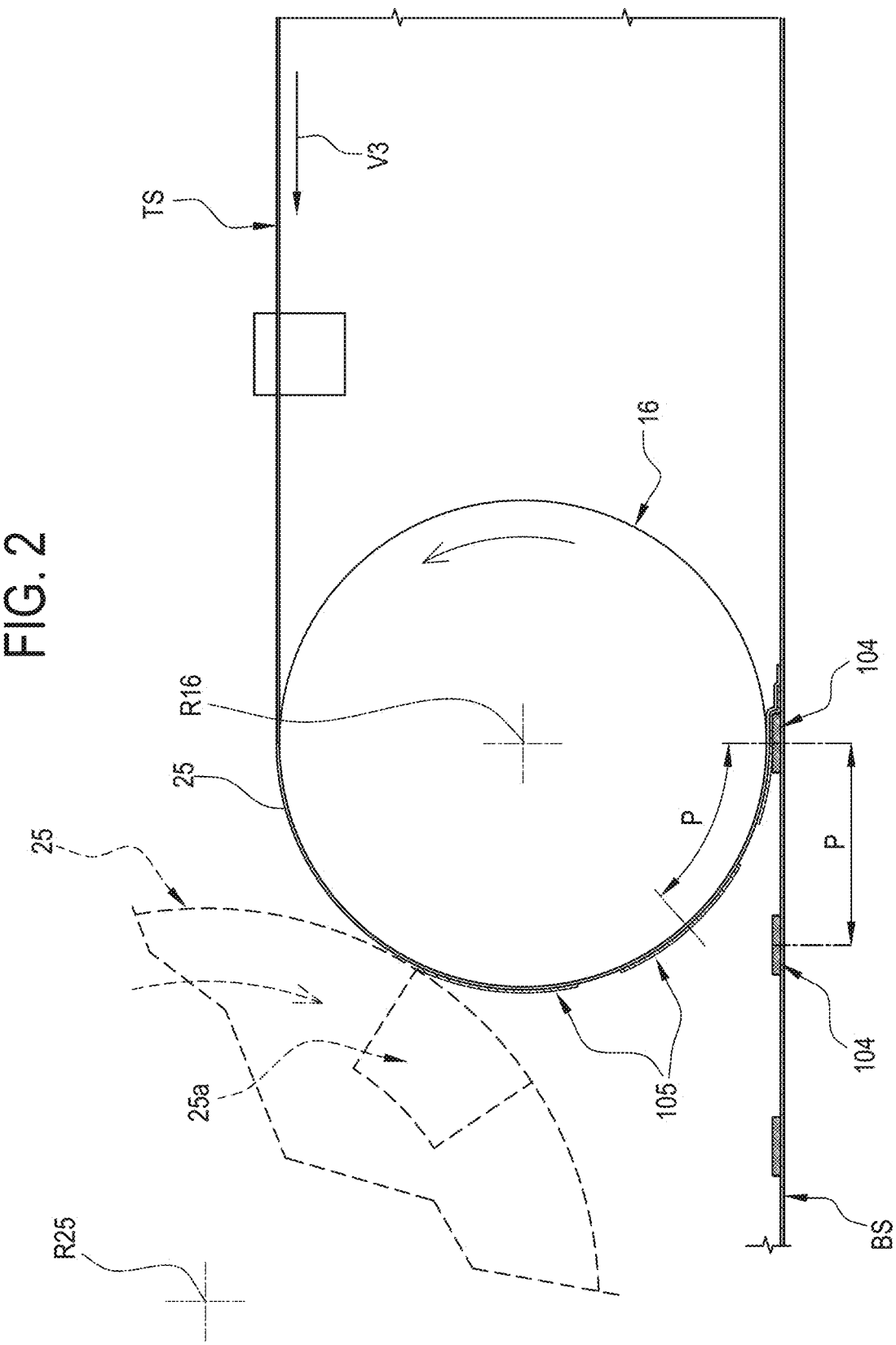
FIG. 2 illustrates a detail of a unit for forming absorbent articles according to this disclosure, in a schematic front view.

The forming unit 1 comprises a unit 3 for forming and positioning the absorbent core 104 and is preferably disposed along the feed path P1 to form and place a succession of first absorbent cores 104 on the web BS. As illustrated in particular in FIG. 2, two consecutive cores 104 on the web BS are spaced by a spacing P which, in practice, is the spacing in the succession of cores 104.

The forming and positioning unit 3 comprises a first and a second mill 4, 5, of substantially known type, for preparing the absorbent material used to make the absorbent cores 104.

The unit 3 comprises a forming drum 6 of substantially known type, which, in the example illustrated, is rotatable clockwise about an axis R6 and which is in communication with the mills 4, 5 to receive a flow of absorbent material on an outer peripheral portion of it.

The absorbent material settles, for example, in suitable suction housings in the form of a plurality of separate cavities, each corresponding to a core 104, aligned with each other and uniformly distributed along the peripheral portion of the drum 6 and capable of holding by suction the absorbent material being carried.

The forming and positioning unit 3 comprises a compression system 7 for compressing the absorbent cores 104 and disposed downstream of the forming drum 6 in a feed direction V2 of the cores 104.

In the embodiment illustrated by way of example, the compression system 7 comprises a first transfer drum 8 for transferring the cores 104, rotatable about an axis R8 and tangent to the drum 6 from which, in use, it receives the cores 104.

A substantially known pressing device 9—for example, a counter-roller—is coupled to the drum 8 in order to compress for a first time the cores 104 advancing thereon.

The system 7 comprises a second transfer drum 10, rotatable about an axis R10, located downstream of the drum 8 and tangent to the latter, from which it receives the cores 104.

In the example illustrated, the compression system 7 comprises a second and a third pressing device 11, 12—for example, counter-rollers—associated with the drum 10 to compress the cores 104 advancing thereon.

In alternative embodiments, the system 7, if present, may comprise different combinations of transfer rollers and related pressing devices, depending, for example, on the compacting requirements of the cores 104.

Downstream of the compression system 7, the unit 3 comprises an accelerator 13, rotatable about an axis R13 and of substantially known type, which picks up the cores 104 from the drum 10 and places them on the web BS at a spacing P in a placing station 14.

The accelerator 13 comprises, for example, a plurality of carrier units 13a, rotating about the axis R13 and each configured to advance a core 104.

The carrier units 13a are tangent to the web BS in the placing station 14 and the directions V2 and V1 coincide; also, the peripheral speed of the accelerator 13 corresponds substantially to the feed speed of the web BS in the station 14.

Preferably, the unit 1 comprises a gluing unit, schematically represented as a block G, upstream of the station 14 in the feed direction V1 of the web BS to spread a layer of glue or adhesive at least to hold the cores 104 in place.

The unit 1 comprises a feed system 15 for feeding a second supporting web TS.

For example, the feed system 15 comprises drums, one of which is a suction drum, illustrated in FIG. 1, labelled 16, rotatable clockwise about an axis R16.

The web TS is intended to form the inner layer 101 of the absorbent article 100 and is, for example, a web of non-woven fabric that will form the topsheet of a diaper.

In an alternative use of the unit 1, the web TS is, for example, a web of non-woven fabric that may become part of an envelope for the absorbent pad 103.

In an alternative use of the unit 1, the web TS is, for example, an impermeable web that may become the backsheet of a diaper.

The web TS advances in a direction V3 along a path P2 which has a curved stretch at the drum 16.

The forming unit 1 comprises a unit 17 for forming and positioning the absorbent core 105 and is preferably disposed along the feed path P2 to form and place a succession of second absorbent cores 105 on the web TS. As illustrated in particular in FIG. 2, two consecutive cores 105 on the web TS are spaced by a spacing P which, in practice, is the spacing in the succession of cores 105.

The forming and positioning unit 17 comprises a first and a second mill 18, 19, of substantially known type, for preparing the absorbent material used to make the absorbent cores 105.

The unit 17 comprises a forming drum 20 of substantially known type, which, in the example illustrated, is rotatable clockwise about an axis R20 and which is in communication with the mills 18, 19 to receive a flow of absorbent material on an outer peripheral portion of it.

The absorbent material settles, for example, in suitable suction housings in the form of a plurality of separate cavities, each corresponding to a core 105, aligned with each other and uniformly distributed along the peripheral portion of the drum 20 and capable of holding by suction the absorbent material being carried.

The forming and positioning unit 17 comprises a compression system 21 for compressing the absorbent cores 105 and disposed downstream of the forming drum 20 in a feed direction V4 of the cores 105.

In the embodiment illustrated by way of example, the compression system 21 comprises a transfer drum 22 for transferring the cores 105, rotatable about an axis R22 and tangent to the drum 20 from which, in use, it receives the cores 105.

In the example illustrated, the compression system 21 comprises two pressing devices 23, 24—for example, counter-rollers—associated with the drum 22 to compress the cores 105 advancing thereon.

In alternative embodiments, the system 21, if present, may comprise different combinations of transfer rollers and related pressing devices, depending, for example, on the compacting requirements of the cores 105.

Downstream of the compression system 21, the unit 17 comprises an accelerator 25, rotatable about an axis R25 and of substantially known type, which picks up the cores 105 from the drum 22 and places them on the web TS at a spacing P in a placing station 26.

The accelerator 25 comprises, for example, a plurality of carrier units 25a, rotating about the axis R13 and each configured to advance a core 105.

The carrier units 25a are tangent to the drum 16 in the placing station 26 and the directions V4 and V3 coincide; also, the peripheral speed of the accelerator 13 substantially corresponds to the feed speed of the web TS, that is, the rotation speed of the drum 16 in the station 26.

Advantageously, in the preferred case, where the web TS is of non-woven fabric, hence permeable, the cores 105 are held on the drum 16 by the suction provided by the latter.

The forming unit 1 comprises a coupling station 27 for coupling the first supporting web BS to the second supporting web TS and disposed downstream of the first placing station 14 and of the second placing station 26.

Each first absorbent core 104 is coupled, in the station 27, to a corresponding second absorbent core 105 in a composite web CT comprising the succession of first absorbent cores 104 and the succession of the second absorbent cores 105 interposed between the first supporting web BS and the second supporting web TS.

In a preferred embodiment, the web BS defines the backsheet 102 of the absorbent article 100 and the web TS, the topsheet 101.

Preferably, the first absorbent core 104 is the small core and the second absorbent core 105 is the big core.

That way, the unit 1 allows making an absorbent article 100 in which the small core 104 is associated with the backsheet and the big core 105 is associated with the topsheet and each big core 105 is positioned on a small core 104 when the topsheet is coupled to the backsheet.

In practice, each big core is positioned on a corresponding small core by the respective supporting webs, thereby overcoming the problems of prior art solutions because, according to this disclosure, the big cores are not released directly onto the small cores and on the web that supports the small cores.

The method for forming the absorbent article 100 according to this disclosure comprises, in a preferred embodiment of it, a step of feeding the first supporting web BS along the feed path P1 in the feed direction V1.

The web BS is, for example, an impermeable web of polyethylene that will form the backsheet of a diaper.

The method comprises a step of placing a succession of first absorbent cores 104 on the first supporting web BS at a spacing P.

Preferably, the absorbent cores 104 will each constitute a small core of a pad 103.

In the example embodiment where the web BS is, in particular, impermeable, the forming method preferably comprises a step of providing an adhesive layer on the first supporting web BS before the step of placing the first absorbent cores 104 on it so that the absorbent cores are held on the web BS as it advances.

Preferably, the absorbent cores 104 are formed in the traditional manner, by feeding the absorbent material, comprising, for example, cellulose pulp and superabsorbent material, to the forming drum 6.

Before being placed on the web BS, the absorbent cores 104 are preferably subjected to compression to give the cores the required density by expelling the air from the absorbent material.

In the example illustrated, the absorbent cores 104 are subjected to compression three times by the pressing devices 9, 11 and 12. In alternative embodiments, compression of the absorbent cores 104 may be omitted or it may be performed in different ways.

When the cores 104 are placed on the web BS, they are suitably spaced at the spacing P in a substantially known manner, for example by means of an accelerator which modifies the spacing of the cores 104 after they have been formed.

Preferably, the cores 104 are spaced after being compressed, making it possible, for example, to vary the size and form of the article 100 made.

In practice, looking at FIG. 1, the web BS is fed in from the left and the absorbent cores 104, after being suitably spaced, are placed on it in the station 14.

The method for forming the absorbent article 100 according to this disclosure comprises, in a preferred embodiment of it, a step of feeding the second supporting web TS along the feed path P2 in the feed direction V3.

The web TS is, for example, a web of non-woven fabric intended to form the topsheet of a diaper.

The method comprises a step of placing a succession of second absorbent cores 105 on the second supporting web TS at a spacing P, corresponding to the spacing P of the absorbent cores 104 on the web BS.

Preferably, the absorbent cores 105 will each constitute a big core of a pad 103 since they are preferably larger than the absorbent cores 104.

Preferably, the absorbent cores 105 are formed in the traditional manner, by feeding the absorbent material, comprising, for example, cellulose pulp and superabsorbent material, to the forming drum 20.

Before being placed on the web TS, the absorbent cores 105 are preferably subjected to compression to give the cores the required density by expelling the air from the absorbent material.

In the example illustrated, the absorbent cores 105 are subjected to compression twice by the pressing devices 23 and 24. In alternative embodiments, compression of the absorbent cores 105 may be omitted or it may be performed in different ways.

When the cores 105 are placed on the web TS, they are suitably spaced at the spacing P in a substantially known manner, for example by means of the accelerator 25 which modifies the spacing of the cores 105 after they have been formed.

Preferably, the cores 105 are spaced after being compressed, making it possible, for example, in particular, to vary the size and form of the article 100 made.

In practice, looking at FIG. 1, the web TS is fed in from the right and the absorbent cores 105, after being suitably spaced, are placed on it in the station 26.

Preferably, the step of placing the succession of second absorbent cores 105 on the second supporting web TS at the spacing P is carried out while the second web TS moves along a curved line, specifically a circular arc which, in the example illustrated, is defined by the drum 16.

That way, the absorbent material which makes up the cores 105 and which is not retained on the web TS does not drop onto the web but is dispersed.

The method according to this disclosure further comprises a step of coupling the first supporting web BS, provided with the absorbent cores 104, to the second supporting web TS, provided with the absorbent cores 105.

The step of coupling is carried out in such a way that each first core 104 is coupled to a corresponding second core 105 in a composite web CT comprising the succession of first absorbent cores 104 and the succession of the second absorbent cores 105 interposed between the first supporting web BS and the second supporting web TS.

Preferably, the step of placing the succession of second absorbent cores 105 on the second supporting web at the spacing P is carried out just before the step of coupling the first supporting web BS to the second supporting web TS, in particular so that as much of the absorbent material of the absorbent cores 105 as possible is able to be held within.

As mentioned, when the first absorbent cores 104 are the small cores and the second absorbent cores 105 are the big cores, the method according to this disclosure allows positioning the big cores 105 on the small cores 104 in the composite web CT without placing the big cores directly on the small cores, thereby obviating the problems of the prior art.

The webs BS and TS are preferably joined by gluing.

In alternative embodiments, they are joined by other joining methods, such as welding, for example.

Preferably, forming method according to this disclosure comprises a step of compressing the composite web CT after the step of coupling the first supporting web BS to the second supporting web TS so as to join the two webs together more effectively and to compact the absorbent pads 103.

In the example illustrated, the directions V1 and V3 are preferably opposite and the webs TS and BS move towards each other in parallel directions.

Preferably, also, the composite web CT moves away from the station 26 along a line parallel to the incoming web TS but in the opposite direction.

Advantageously, the absorbent cores 104, for example, the small cores, and the absorbent cores 105, for example, the big cores, are coupled to separate webs, for example, to the first web BS and to the second web TS. This minimizes the positioning and joining problems, as well as the problems connected with dispersal of the absorbent material.

The supporting webs BS and TS are thus effectively synchronized when they are joined to each other, so as to make multilayer pads 103 that are well "wrapped" in the composite web CT.

As mentioned, in a preferred embodiment, the composite web CT is made up of the topsheet, the backsheet and the multilayer pads of the nappies and undergoes further processing for forming and packaging the nappies.

The multilayer pads are preferably of the type comprising a small core and a big core which, in use, is directed towards the wearer.

In an embodiment, and depending on the materials used, the absorbent article made in the unit 1 is an absorbent pad which comprises a big core and a small core and which is sandwiched between two webs of non-woven fabric.

In an embodiment, the big cores, which are joined to the respective supporting web, are positioned on the small cores, which have been previously joined to the respective supporting web.

In an embodiment, the small cores, which are joined to the respective supporting web, are positioned on the big cores, which have been previously joined to the respective supporting web.

Joining the absorbent cores first to the supporting webs and then to each other makes it possible to obviate the problems of positioning one set of cores on top of the other set and holding them in place.

What is claimed is:

1. A method for forming an absorbent article comprising a first absorbent core and a second absorbent core which are superposed on each other, the forming method comprising:
    a step of feeding a first supporting web along a first feed path in a first feed direction;
    a step of placing a succession of first absorbent cores on the first supporting web at a preset spacing;
    a step of feeding a second supporting web along a second feed path in a second feed direction;
    a step of placing a succession of second absorbent cores on the second supporting web at the preset spacing;
    a step of coupling the second supporting web to the first supporting web in such a way that each first absorbent core is coupled to a corresponding second absorbent core in a composite web comprising the succession of first absorbent cores and the succession of the second absorbent cores interposed between the first supporting web and the second supporting web;
    compressing the first absorbent cores before the step of placing the succession of first absorbent cores on the first supporting web.

2. The method according to claim 1, comprising a step of accelerating each of the first absorbent cores before the step of placing the succession of first absorbent cores on the first supporting web, so as to space the first absorbent cores by the preset spacing.

3. The method according to claim 2, wherein the step of compressing the first absorbent cores is carried out before the step of accelerating each of the first absorbent cores.

4. The method according to claim 1, comprising a step of compressing the second absorbent cores before the step of placing the succession of second absorbent cores on the second supporting web.

5. The method according to claim 4, comprising a step of accelerating each of the second absorbent cores before the step of placing the succession of second absorbent cores on the second supporting web, so as to space the second absorbent cores by the preset spacing.

6. The method according to claim 1, wherein the step of compressing the second absorbent cores is carried out before the step of accelerating each of the second absorbent cores.

7. The method according to claim 1, comprising a step of compressing the composite web after the step of coupling the first supporting web to the second supporting web.

8. The method according to claim 1, wherein the step of placing the succession of second absorbent cores on the second supporting web at the preset spacing is carried out while the second supporting web moves along a circular arc.

9. The method according to claim 1, wherein the step of placing the succession of second absorbent cores on the second supporting web at the preset spacing is carried out just before the step of coupling the first supporting web to the second supporting web.

10. The method according to claim 1, comprising a step of providing an adhesive layer on the first supporting web before the step of placing the first absorbent cores on the first supporting web.

11. The method according to claim 1, wherein the first absorbent cores are smaller than the second absorbent cores.

12. The method according to claim 11, wherein each second absorbent core of the second absorbent cores is placed on top of a corresponding first absorbent core of the first absorbent cores during the step of coupling the second supporting web to the first supporting web.

13. The method according to claim 1, wherein at least a portion of the second feed path is parallel to the first feed path and the second feed direction is opposite to the first feed direction at least where the first feed path and the at a least a portion of the second feed path are parallel.

14. A method for forming an absorbent article comprising a first absorbent core and a second absorbent core which are superposed on each other, the forming method comprising:

a step of feeding a first supporting web along a first feed path in a first feed direction;

a step of placing a succession of first absorbent cores on the first supporting web at a preset spacing;

a step of feeding a second supporting web along a second feed path in a second feed direction;

a step of placing a succession of second absorbent cores on the second supporting web at the preset spacing;

a step of coupling the second supporting web to the first supporting web in such a way that each first absorbent core is coupled to a corresponding second absorbent core in a composite web comprising the succession of first absorbent cores and the succession of the second absorbent cores interposed between the first supporting web and the second supporting web;

compressing the second absorbent cores before the step of placing the succession of second absorbent cores on the second supporting web.

15. The method according to claim 1, wherein the first supporting web is an impermeable backsheet of an absorbent article and the second supporting web is a topsheet of the absorbent article.

* * * * *